US00PP12896P2

(12) United States Plant Patent
Bradford

(10) Patent No.: US PP12,896 P2
(45) Date of Patent: Aug. 27, 2002

(54) PEACH TREE NAMED 'AUGUST PRINCESS'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 5 days.

(21) Appl. No.: 09/813,381

(22) Filed: Mar. 22, 2001

(51) Int. Cl.[7] ..... A01H 5/00
(52) U.S. Cl. ..... Plt./195
(58) Field of Search ..... Plt./195

(56) References Cited

U.S. PATENT DOCUMENTS

PP6,363 P 11/1988 Bradford et al.
PP9,515 P 4/1996 Bradford et al.

*Primary Examiner*—Bruce R. Campell
*Assistant Examiner*—Susan B. McCormick

(57) ABSTRACT

The present invention relates to a peach tree, *Prunus persica,* and more particularly to a new and distinct variety broadly characterized by a large size, vigorous, hardy, self-fertile, productive and regular bearing tree. The fruit matures under the ecological conditions described approximately the third week in August, with first picking on Aug. 20, 2000. The fruit is uniformly large in size, very good in flavor, globose in shape, clingstone in type, firm in texture, white in flesh color, and mostly red in skin color. The variety was developed as a first generation cross using August Red (U.S. Plant Pat. No. 6,363) yellow flesh nectarine as the selected seed parent and White Princess (U.S. Plant Pat. No. 9,515) peach as the selected pollen parent.

1 Drawing Sheet

BACKGROUND OF THE VARIETY

In a continuing effort to improve the quality of shipping fruits, I, the inventor, typically hybridize a large number of nectarine, peach, plum, apricot, and cherry seedlings each year. The present invention relates to a new and distinct variety of peach tree, botanical name *Prunus persica* cultivar 'August Princess'. The present variety was hybridized by me in 1991, grown as a seedling on its own root in my greenhouse, and transplanted to a cultivated area of our experimental orchard at Bradford Farms near Le Grand, Calif. in Merced County (San Joaquin Valley). It was developed as a first generation cross using August Red (U.S. Plant Pat. No. 6,363) yellow flesh nectarine as the selected seed parent and White Princess (U.S. Plant Pat. No. 9,515) peach as the selected pollen parent. Subsequent to origination of the present variety of peach tree, I asexually reproduced it by budding and grafting in the experimental orchard described above, and such reproduction of plant and fruit characteristics were true to the original plant in all respects. The reproduction of the variety included the use of Nemaguard Rootstock (unpatented) upon which the present variety was compatible and true to type.

The present variety is similar to its selected seed parent, August Red (U.S. Plant Pat. No. 6,363) peach, by producing clingstone fruit that ripens in the latter part of August and is globose in shape, firm in texture, and mostly red in skin color, but is distinguished therefrom and an improvement thereon by producing fruit that is white instead of yellow in flesh color, that is subacid instead of acid in flavor, and that is peach instead of nectarine.

The present variety is most similar to its pollen parent, White Princess (U.S. Plant Pat. No. 9,515) peach, by producing peaches that are white in flesh color, subacid and sweet in flavor, and mostly red in skin color, but is distinguished therefrom and an improvement thereon by producing fruit that is clingstone instead of freestone, that is larger in size, and that matures about ten days later.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of peach tree, the following has been observed of an 8 year-old tree grown under the ecological conditions prevailing near Le Grand, Merced County (San Joaquin Valley), Calif., and was developed at the state of firm ripe on Aug. 24, 2000. All major color code designations are by reference to the Inter-Society Color Council, National Bureau of Standards. Common color names are also used occasionally.

TREE

Size: Large, reaching and maintaining a height of 12' [3.66 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Production: Very productive, thinning necessary.

Fertility: Self-fertile.

Bearing: Regular bearer with no alternate bearing yet observed.

Trunk:

*Size.*—Medium, reaching a maximum diameter of 6.5" [165 mm.] after the eighth growing season.

*Texture.*—Shaggy.

*Bark color.*—Grayish brown [61. gy.Br].

*Lenticels.*—Numerous. Color: Moderate orange yellow [71. m.OY]. Typical Size: 1/8" to 3/8" [3.2–9.5 mm.].

Branches:

*Size.*—Diameter of scaffold is 3¾" [95 mm.] measured 12" above the crotch. Medium, typical of *Prunus persica*.

*Texture.*—Smooth on 1st year wood, increasing roughness with age.

*Color.*—1st Year Wood Topside: Grayish red [19. gy.R]. 1st Year Wood Underside: Light yellow green [119. l.YG]. Older Wood: Moderate brown [58. m.Br].

*Lenticels.*—Numerous. Color: Deep orange yellow [69. deep OY]. Average Size: 1/32" to 1/16" [0.8–1.6 mm.].

Leaves:

*Size.*—Large. Average Length: 5½" [140 mm.]. Average Width: 1 11/16" [43 mm.].

*Arrangement.*—Alternate.

*Thickness.*—Medium.

*Form.*—Elliptical.

*Apex.*—Acuminate.

*Base.*—Acute.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Light yellow green [119. l.YG].

*Stipules.*—Numerous, 2 per leaf, up to 6 per growing tip. Average Length: ¼" [6.4 mm.].

*Glands.*—Numbers: 1 to 4 per leaf. Position: Usually opposite, occasionally alternate, positioned both on the petiole and the base of blade. Size: Small. Form: Globose. Color: Light yellow green [119. l.YG].

*Leaf buds.*—Pointed.

Flower buds:

*Hardiness.*—Hardy, with respect to central California winters.

*Diameter.*—Typically 3/8" [9.5 mm.] 1 week before bloom.

*Length.*—Typically ¾" [19.1 mm.] 1 week before bloom.

*Form.*—Not appressed.

*Surface.*—Pubescent.

*Color.*—Moderate purplish red [258. m.pR].

Flowers: Perfect, complete, perigynous, usually a single pistil, typically thirty or more stamens, five sepals and petal locations alternately positioned.

*Type.*—Showy.

*Average flower diameter.*—1 9/16" [39.7 mm.].

*Number of petals.*—Usually five, very few doubles.

*Petal shape.*—Rounded.

*Petal margin.*—Slightly wavy.

*Average petal diameter.*—5/8" [15.9 mm.].

*Petal color.*—Pale purplish pink [252. p.pPk].

*Anther color.*—Moderate purplish red [258. m.pR].

*Stigma color.*—Light yellow green [119. l.YG].

*Sepal color.*—Dark grayish red [20. d.gy.R].

*Sepal length.*—3/16" [4.8.].

*Sepal width.*—5/32" [4.0 mm.].

*Average pistil length.*—9/16" [14.3 mm.].

*Average stamen length.*—9/16" [14.3 mm.].

*Fragrance.*—Moderate when nectar is present.

*Blooming period.*—Medium compared with other varieties.

*Onset of bloom.*—One percent on Mar. 2, 2001.

*Duration of bloom.*—One to two weeks, dependent on ambient temperature.

*Number per cluster.*—Generally 1, occasionally 2 or more.

FRUIT

Maturity when described: Firm ripe, Aug. 24, 2000.

Date of first picking: Aug. 20, 2000.

Date of last picking: Sep. 1, 2000.

Size: Uniform, large.

*Average diameter axially.*—3 5/16" [84.1 mm.].

*Average diameter across suture plane.*—3 3/8" [85.7 mm.].

*Typical weight.*—10 ounces [283 grams].

Form: Uniform, symmetrical, globose.

*Longitudinal section form.*—Round.

*Transverse section through diameter.*—Round.

Suture: An inconspicuous line extending from the base that becomes a shallow groove toward the apex and has a marked depression just beyond the pistil point.

Ventral surface: Strongly rounded, lipped toward the apex on both sides.

Lips: Equal.

Cavity: Flaring, elongated in the suture plane, suture showing on both sides with Pale yellow green [121. p.YG] stem markings typical.

*Depth.*—7/8" [22.2 mm.].

*Breadth.*—1 5/16" [33.3 mm.].

Base: Rounded.

Apex: Rounded.

Pistil point: Mostly apical, slightly mammiform.

Stem: Medium.

*Average length.*—3/8" [9.5 mm.].

*Average width.*—3/16" [4.8 mm.].

Skin:

*Thickness.*—Medium.

*Texture.*—Medium.

*Tenacity.*—Tenacious to flesh.

*Astringency.*—None.

*Tendency to crack.*—None observed.

*Color.*—Dark red [16. d.R] smoothly blending into a Moderate pink [5. m.Pk] background with occasional Yellowish white [92. yWhite] sun protected areas.

Down: Scant, short, does not roll up when rubbed.

Flesh:

*Color.*—Yellowish white [92. yWhite] with some Dark red [16. d.R] streaking close to the stone and Dark red [16. d.R] flecking toward the skin.

*Surface of pit cavity.*—Dark red [16. d.R] fibers breaking when twisted from the stone.

*Amygdalin.*—Scarce.

*Juice.*—Abundant, rich.

*Texture.*—Firm, crisp.

*Fibers.*—Abundant, fine.

*Ripens.*—Slightly earliest toward the apex and along the lips.

*Flavor.*—Subacidic and sweet, typically 16 brix.

*Aroma.*—Slight.

*Eating quality.*—Very good.

STONE

Type: Clingstone.
Form: Oval.
Base: Straight.
Apex: Acute.
Sides: Equal.
Surface: Irregularly furrowed near the apex and pitted toward the base.
Ridges: Jagged toward the base.
Color: Dark grayish reddish brown [47. d.gy.rBr].
Average pit wall thickness: ¼" [6.4 mm.].
Average width: 15/16" [23.8 mm.].
Average length: 1 5/16" [33.3 mm.].
Tendency to split: None observed.
Kernel:
*Form.*—Oval.
*Color.*—Brilliant yellow [83. brill.Y] when first removed with Dark yellowish brown [78. d.yBr] veins.
*Taste.*—Bitter.
*Viable.*—Yes.
*Average width.*—½" [12.7 mm.].
*Average length.*—11/16" [17.5 mm.].
Pellicle color: Dark yellowish brown [78. d.yBr].
Amygdalin: Abundant.

USE

Market: Fresh and long distance shipping.
Keeping quality: Fruit quality observed to remain in good condition in excess of 20 days in standard cold room at 36° Fahrenheit [2° Celsius].
Resistance to insects: No unusual susceptibilities noted.
Resistance to diseases: No unusual susceptibilities noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its pollen parent, White Princess (U.S. Plant Pat. No. 9,515) peach, by producing peaches that are white in flesh color, firm in texture, subacid and sweet in flavor, and mostly red in skin color, but is distinguished therefrom and an improvement thereon by producing fruit that is clingstone instead of freestone, that is larger in size, and that matures about ten days later.

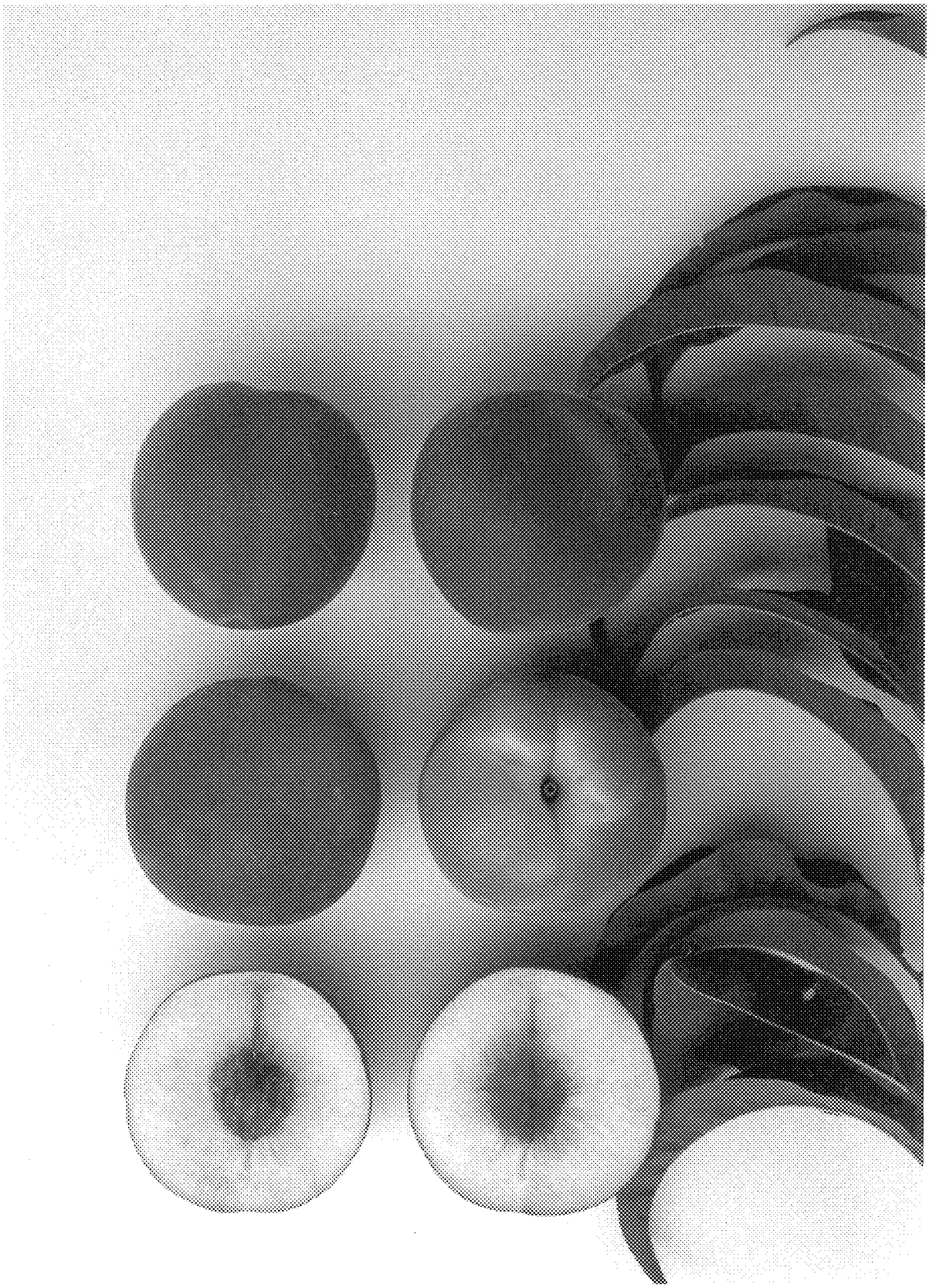

* * * * *